US012611482B2

(12) United States Patent (10) Patent No.: US 12,611,482 B2

Cronin et al. (45) Date of Patent: Apr. 28, 2026

(54) AIR SANITIZER

(71) Applicant: NUALIGHT LIMITED, Cork (IE)

(72) Inventors: Andrew Cronin, Haywards Heath (GB); Ben Cole, Crawley (GB); Brian Norris, Haywards Heath (GB)

(73) Assignee: Nualight Limited, Cork (IE)

( * ) Notice: Subject to any disclaimer, the term of this patent is extended or adjusted under 35 U.S.C. 154(b) by 646 days.

(21) Appl. No.: 17/925,136

(22) PCT Filed: Jul. 2, 2021

(86) PCT No.: PCT/EP2021/068366

§ 371 (c)(1),
(2) Date: Nov. 14, 2022

(87) PCT Pub. No.: WO2022/008380

PCT Pub. Date: Jan. 13, 2022

(65) Prior Publication Data

US 2023/0181788 A1 Jun. 15, 2023

(30) Foreign Application Priority Data

Jul. 6, 2020 (EP) ..................................... 20184128

(51) Int. Cl.
A61L 9/20 (2006.01)
A47F 3/04 (2006.01)

(52) U.S. Cl.
CPC ............ A61L 9/205 (2013.01); A47F 3/0447 (2013.01); A61L 2209/12 (2013.01)

(58) Field of Classification Search
CPC ..... A61L 9/205; A61L 2209/12; A47F 3/0447
See application file for complete search history.

(56) References Cited

U.S. PATENT DOCUMENTS

| | | | |
|---|---|---|---|
| 7,540,162 B2 | 6/2009 | Nordstrom | |
| 9,066,988 B1 | 6/2015 | Burnett | |
| 9,586,460 B2 * | 3/2017 | Gross | F24F 8/192 |
| 11,771,795 B2 * | 10/2023 | Kim | B01D 53/007 |
| | | | 422/121 |
| 2004/0241040 A1 | 12/2004 | Wei et al. | |

(Continued)

FOREIGN PATENT DOCUMENTS

| | | | |
|---|---|---|---|
| CA | 2711838 A1 * | 2/2011 | A61L 9/205 |
| CN | 206 406 730 U | 8/2017 | |

(Continued)

OTHER PUBLICATIONS

Mei; A Low-concentration Formaldehyde In The Air Purifier; CN-208431874-U (Year: 2019).*

(Continued)

*Primary Examiner* — Regina M Yoo

(74) *Attorney, Agent, or Firm* — Studebaker Bracket PLLC

(57) ABSTRACT

A sanitizer has substrates which are coated with an optically-activated nanomaterial TiO2 coating for cleaning air which comes into contact with the surfaces of the coating. UV LED light sources are arranged to emit light to be incident on the surfaces to activate the coatings. There is a large surface for impingement of air on the coatings due to a grille arrangement of the substrates, and the LED-emitted UV light being incident at acute angles on the grille honeycomb structure.

17 Claims, 15 Drawing Sheets

(56) References Cited

U.S. PATENT DOCUMENTS

| | | | | |
|---|---|---|---|---|
| 2010/0129267 A1* | 5/2010 | Akutsu | .................. | A61L 9/205 |
| | | | | 422/121 |
| 2013/0028796 A1* | 1/2013 | Nakatani | ........... | B01D 53/8603 |
| | | | | 422/121 |
| 2018/0133355 A1* | 5/2018 | Kirschman | ............... | A61L 2/08 |
| 2018/0147313 A1* | 5/2018 | Cheng | ..................... | B01J 35/57 |
| 2020/0345887 A1* | 11/2020 | Kim | ........................ | D06F 58/20 |
| 2022/0404045 A1* | 12/2022 | Park | ......................... | A61L 9/20 |

FOREIGN PATENT DOCUMENTS

| | | | | | |
|---|---|---|---|---|---|
| CN | 206 522 859 U | 9/2017 | | | |
| CN | 208 431 874 U | 1/2019 | | | |
| CN | 110 038 425 A | 7/2019 | | | |
| JP | 2004 073265 A | 3/2004 | | | |
| KR | 200291750 Y1 * | 10/2002 | ............. | A61L 9/205 |
| WO | WO-2014128673 A1 * | 8/2014 | ............... | F24F 8/30 |
| WO | WO-2019147058 A1 * | 8/2019 | ............... | F24F 8/24 |

OTHER PUBLICATIONS

English translation of WO2019147058 (Year: 2019).*
International Search Report issued in PCT/EP2021/068366; mailed
Jan. 20, 2022.

* cited by examiner

1

24

24

DETAIL A
SCALE 1 : 1

A

AIR SANITIZER

INTRODUCTION

The invention relates to air cleaning for rooms, or display cases or cabinets including refrigerated food and drink retail display cases.

U.S. Pat. No. 7,540,162 describes a display case with air flow paths for circulating air around one or more objects displayable in a display area in the display case, and ultraviolet (UV) radiation elements in the air paths for sanitizing the circulating air to reduce airborne contaminants. There is a lower trough area to catch debris falling from the display area.

The present invention is directed towards providing improved air cleaning.

SUMMARY OF THE INVENTION

We describe an air sanitizer comprising:

a housing with an air inlet and an air outlet;

substrates coated with a photo-catalytic coating for cleaning air which comes into contact with the surfaces of the coating, and a light source comprising LEDs arranged to emit light to be incident on said surfaces to activate the coating.

Preferably, the substrates are arranged as at least one grille. Preferably, there are an upstream grille and a downstream grille in a direction of air flow. Preferably, the LEDs are mounted between said grilles, to emit light across an air flow direction to include the grilles in their fields of emission.

Preferably, the light source is a UV light source and the coating comprises $TiO_2$. Preferably, at least some of the LEDs emit with a wavelength in the range of 320 nm to 440 nm, preferably 320 to 400 nm.

Preferably, the LEDs include LEDs of different wavelengths, optionally 380 nm and 400 nm. Preferably, the LEDs are arranged to emit light which is directly incident on some of said substrate surfaces, and indirectly incident by way of reflection on other substrate surfaces.

Preferably, the surfaces are on a plurality of substrates which are substantially orthogonal to an optical axis of the light source, but are spaced from said axis so that diverging light is directly incident on at least some of the surfaces and at least some reflect to be incident on other substrate surfaces. Preferably, the light emission is at an acute angle to orthogonal to an air flow path between a plurality of substrates. Preferably, in at least some of the LEDs have an angle of emission across +45° to −45°.

Preferably, the substrates are in the form of a mesh having an array of air flow conduits extending substantially in an air flow direction. Preferably, at least some of the conduits are polygonal in cross-sectional shape. Preferably, at least some of the conduits are hexagonal, providing a honeycomb structure. Preferably, the substrates have a thickness in the range of 5 μm to 25 μm. Preferably, the substrates are separated by an internal air flow path in the range of 5 cm to 50 cm, preferably 5 cm to 20 cm.

In some examples, the sanitizer is adapted for stand-alone operation, comprising at least one fan mounted upstream of said substrates. Preferably, the sanitizer comprises a particulate filter upstream of said substrates.

Preferably, the filter has a cone shape, mounted symmetrically about a longitudinal axis of air flow and narrowing in an air flow downstream direction. Preferably, the filter is a high efficiency particulate absorbing (HEPA) filter.

Preferably, the sanitizer inlet is annular around an air flow longitudinal axis. Preferably, the inlet is formed by a gap between a base and a housing main body, which preferably have a round cross-sectional shape. Preferably, there are a plurality of fans arranged on and around a longitudinal air flow axis.

Preferably, the outlet is annular around an air flow longitudinal axis. Preferably, the sanitizer comprises a sub-assembly of components which are interconnected and removable from the housing, said components comprising a fan, a filter, said LEDs, and said substrates.

Preferably, the sub-assembly is interconnected by a plurality of arms which extend parallel to a housing longitudinal axis. Preferably, the arms are adjacent to an internal surface of the housing.

Preferably, the sub-assembly comprises at least one bracket which maintains an axial separation between a plurality of spaced-apart substrates and also a gap between said substrates and the housing internal surface. Preferably, the LEDs are mounted to emit UV light incident on the substrates and also on the housing internal surface for reflection from said internal surface to the substrates.

In some examples, the sanitizer has a substantially rectangular box shape, with a depth dimension wish is less than a width dimension, and the width dimension is less than a length dimension, and the light sources are mounted to emit across the width dimension and the substrates are mounted for air flow through the depth dimension.

The sanitizer may comprise mounting fixtures for mounting to a cooler with a fan.

We also describe a cabinet or display case comprising a housing for supporting shelves for placement of products, a cooler with a fan for circulating air and delivering cooled air around said products, and a sanitizer mounted in an air path to or from the cooler. Preferably, the sanitizer is mounted at an inlet of the cooler. Preferably, the cooler and the sanitizer are in a chamber underneath a product volume, being separated by a floor. Preferably, said floor is planar for ease of cleaning.

Additional Statements

We describe an air sanitizer comprising:

a housing with an air inlet and an air outlet, and being arranged to be mounted in an air flow;

substrates coated with a photo-catalytic coating for cleaning air which comes into contact with the surfaces of the coating, and a light source arranged to emit light to be incident on said surfaces to activate the coatings.

Preferably, at least one of the inlet and the outlet are formed by a grille of said substrates. Preferably, both of said inlet and outlet are formed by said grilles. Preferably, the light source is a UV light source.

Preferably, the light source comprises an array of at least one LED. Preferably, at least some of the LEDs emit with a wavelength in the range of 320 nm to 400 nm. Preferably, the LEDs include LEDs of different wavelengths.

Preferably, the light source is arranged to emit light which is directly incident on some of said surfaces, and indirectly incident by way of reflection on other surfaces.

Preferably, the surfaces are on a plurality of substrates which are substantially orthogonal to an optical axis of the light source, but are spaced from said axis so that diverging light is directly incident on at least some of the surfaces. Preferably, at least some of the LEDs have an angle of emission across +45° to −45°.

Preferably, the substrates form opposed sides of the sanitizer, through which air flows, and the light emission is substantially orthogonal to a path between the opposed substrates.

Preferably, the substrates are in the form of a mesh having an array of air flow conduits (29) extending substantially in an air flow direction. Preferably, at least some of the conduits are polygonal in cross-sectional shape. Preferably, at least some of the conduits are hexagonal, providing a honeycomb structure.

Preferably, the substrates have a thickness in the range of 5 μm to 25 μm. Preferably, the sanitizer has a substantially rectangular box shape, with a depth dimension wish is less than a width dimension, and the width dimension is less than a length dimension, and the light sources are mounted to emit across the width dimension and the substrates are mounted for air flow through the depth dimension. Preferably, the substrates are separated by an internal air flow path in the range of 5 cm to 50 cm, preferably 5 cm to 20 cm.

Preferably, the sanitizer comprises mounting fixtures (23) for mounting to a cooler (30, 40) with a fan.

We also describe a cabinet or display case comprising a housing for supporting shelves for placement of products, a cooler with a fan for circulating air and delivering cooled air around said products, and a sanitizer as described herein mounted in an air path to or from the cooler.

Preferably, the sanitizer is mounted at an inlet of the cooler. Preferably, the cooler and the sanitizer are in a chamber underneath a product volume, being separated by a floor. Preferably, said floor is planar for ease of cleaning.

DETAILED DESCRIPTION OF THE INVENTION

The invention will be more clearly understood from the following description of some embodiments thereof, given by way of example only with reference to the accompanying drawings in which.

A photocatalytic air sanitizer or purifier is used in one example in a refrigerated display case which provides an air flow or air curtain to ensure that cool air is recirculated within the display. The recycled air is open to contamination from airborne suspended particles such as bacteria, micro-organisms, viruses and volatile organic compounds. This would result in risk of odours, food spoilage, and food contamination. However, the air is continuously purified by the photocatalytic air purifier within the display case. The air purifier is modular and is mounted in-line with air cooling components, in one example upstream of a fan and air-cooling tubes mounted underneath a display compartment.

In other examples the system may alternatively be a cold room with recirculating air, or any other air circulating systems such as for hotels, bakeries, or abattoirs. However, the apparatus is particularly suited to cabinets.

Figure 1:
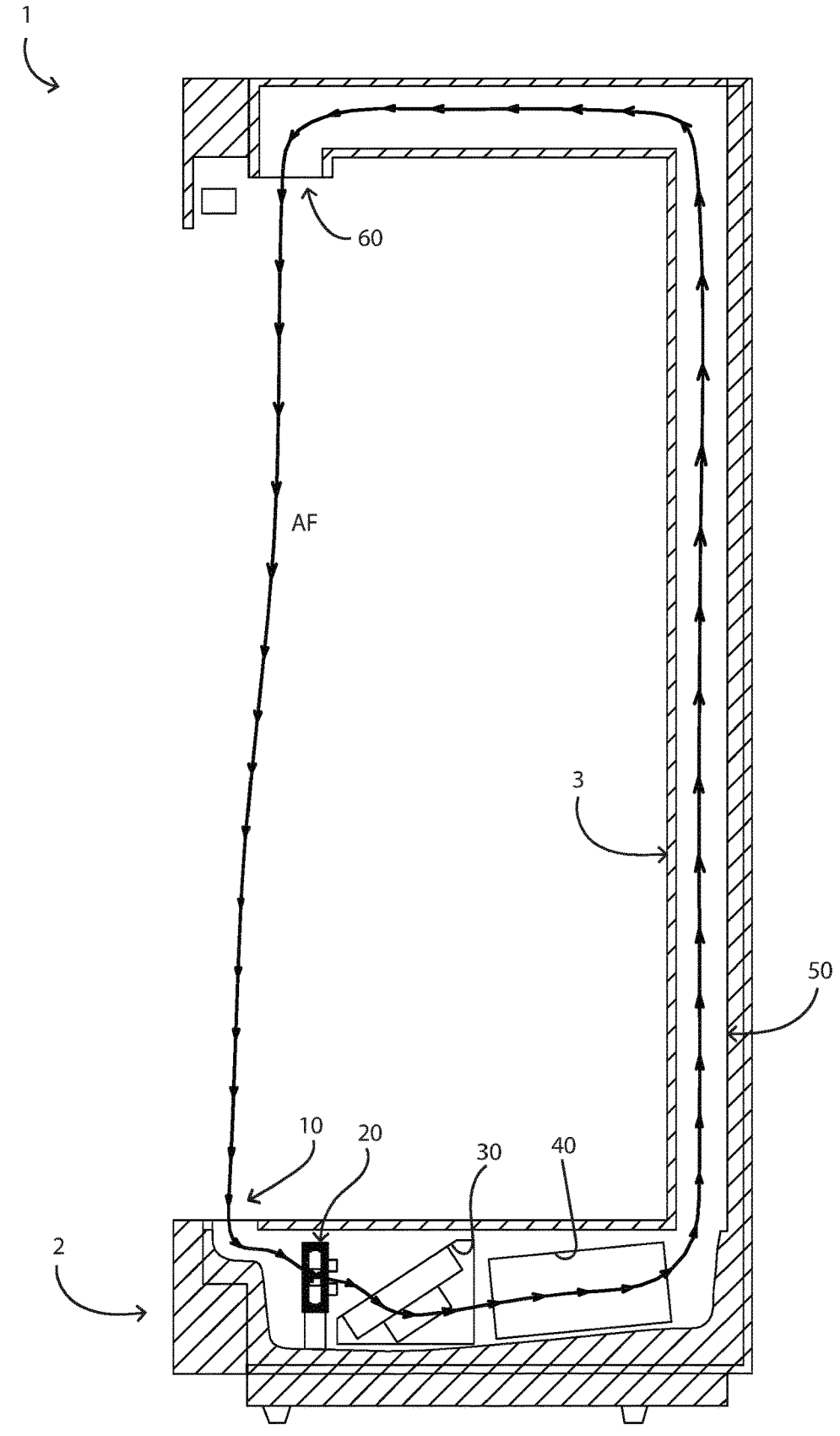
FIG. 1 is a cross-sectional side view of a refrigerated display case.
Figure 2:
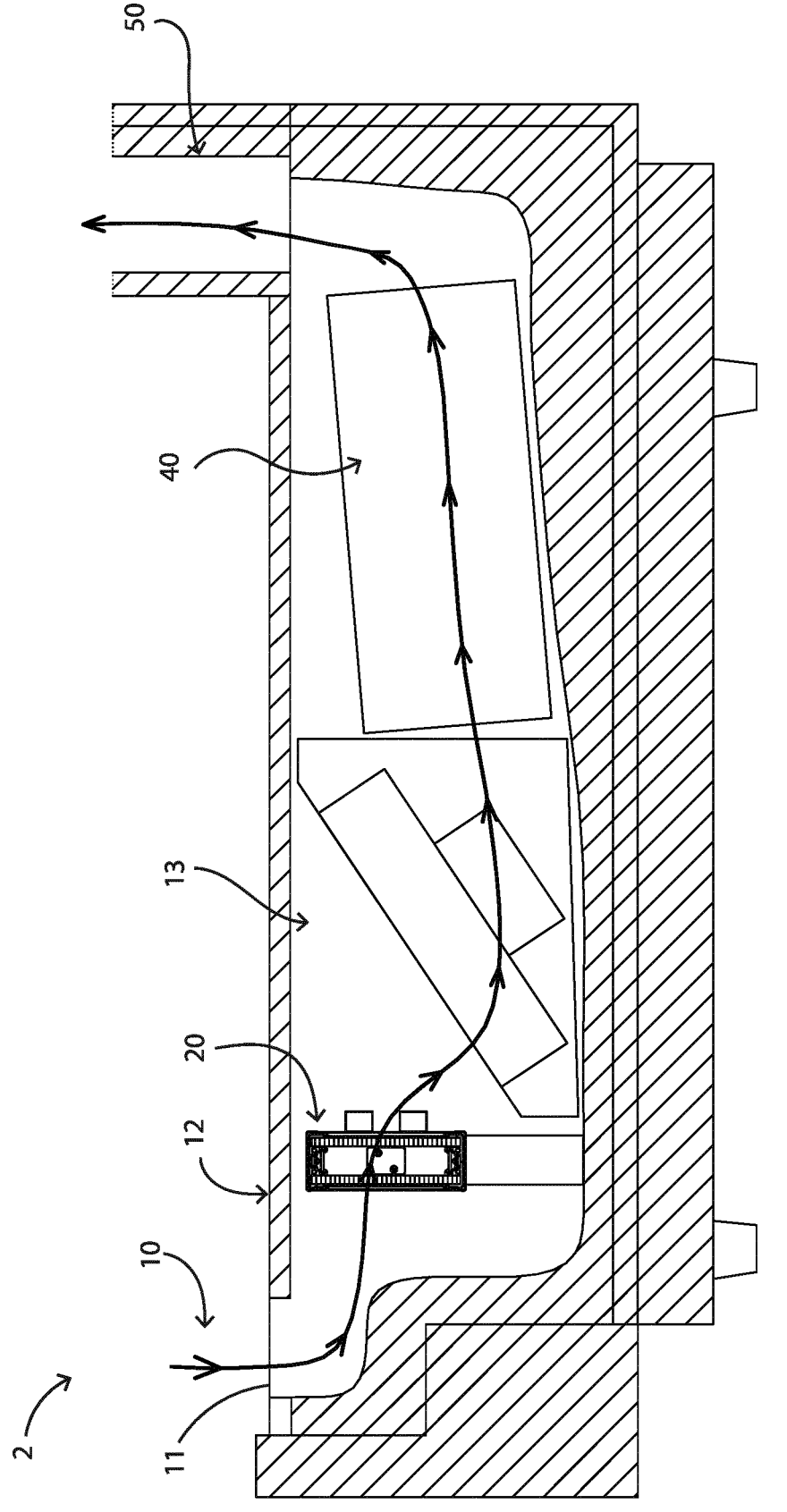
FIG. 2 is an enlarged view showing an air management system of the case and the general direction of air flows, the system having an air cooler and an air sanitizer mounted for in-line flow.

In more detail. referring to FIGS. 1 and 2 a refrigerated retail display case or cabinet 1 comprises a base 2 and a rear wall 3. The base 2 comprises an air inlet 10 which draws in air from the volume around displayed items in the case 1, from where it flows through a sanitizer or purifier 20, a fan 30, and a cooler 40. From there, the air flows upwardly through conduits 50 within the rear wall 3 for flow through an outlet 60 to flow around displayed goods on display shelves (not shown). This provides impingement of cool and sanitized air around items.

The air is drawn through an inlet comprising a small opening grille 11 across the front floor of the case 1. The floor comprises a floor panel 12 which is planar and is easily cleaned of debris which falls from above, and it prevents debris from getting into the air handling components underneath. FIG. 2 shows the generalized air flows.

The fan 30 and the cooler 40 are of conventional construction, and may be of any suitable specification to suit the air handling requirements of the case as is known in the art.

Figure 3:
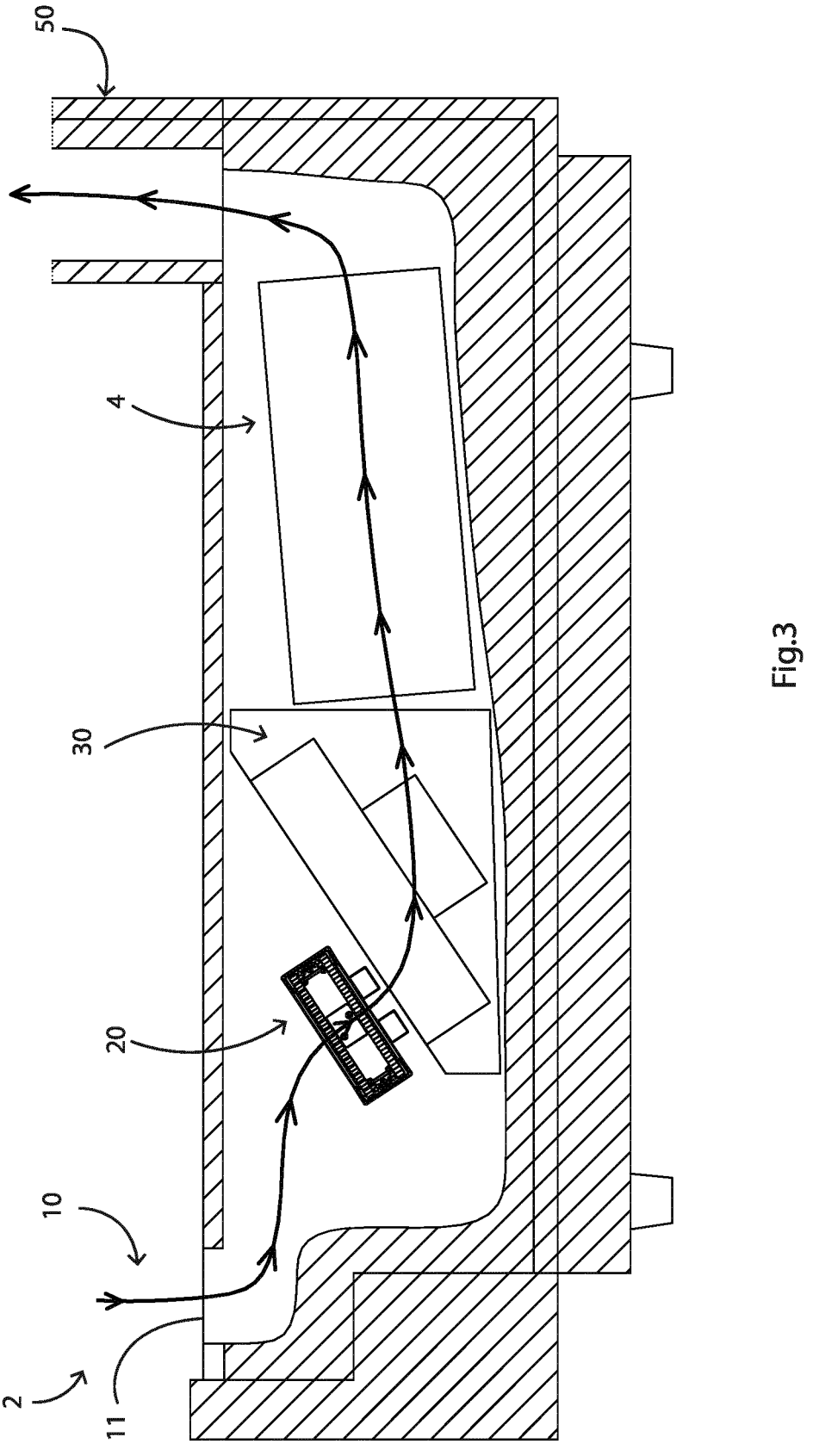
FIG. 3 is a similar view with the sanitizer at a different orientation on the air cooler.
Figure 4:
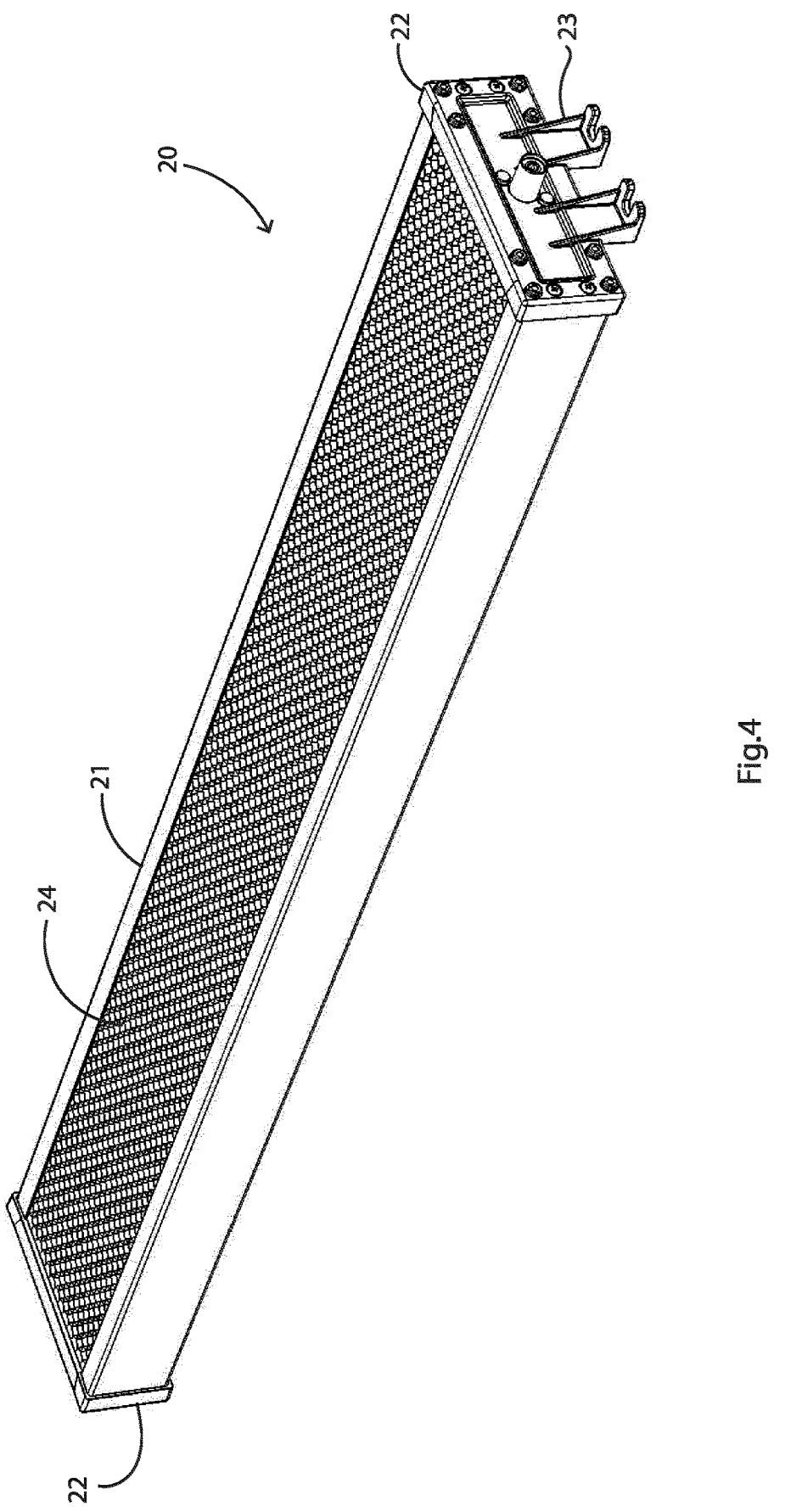
FIG. 4 is a perspective view of the sanitizer.
Figure 5:
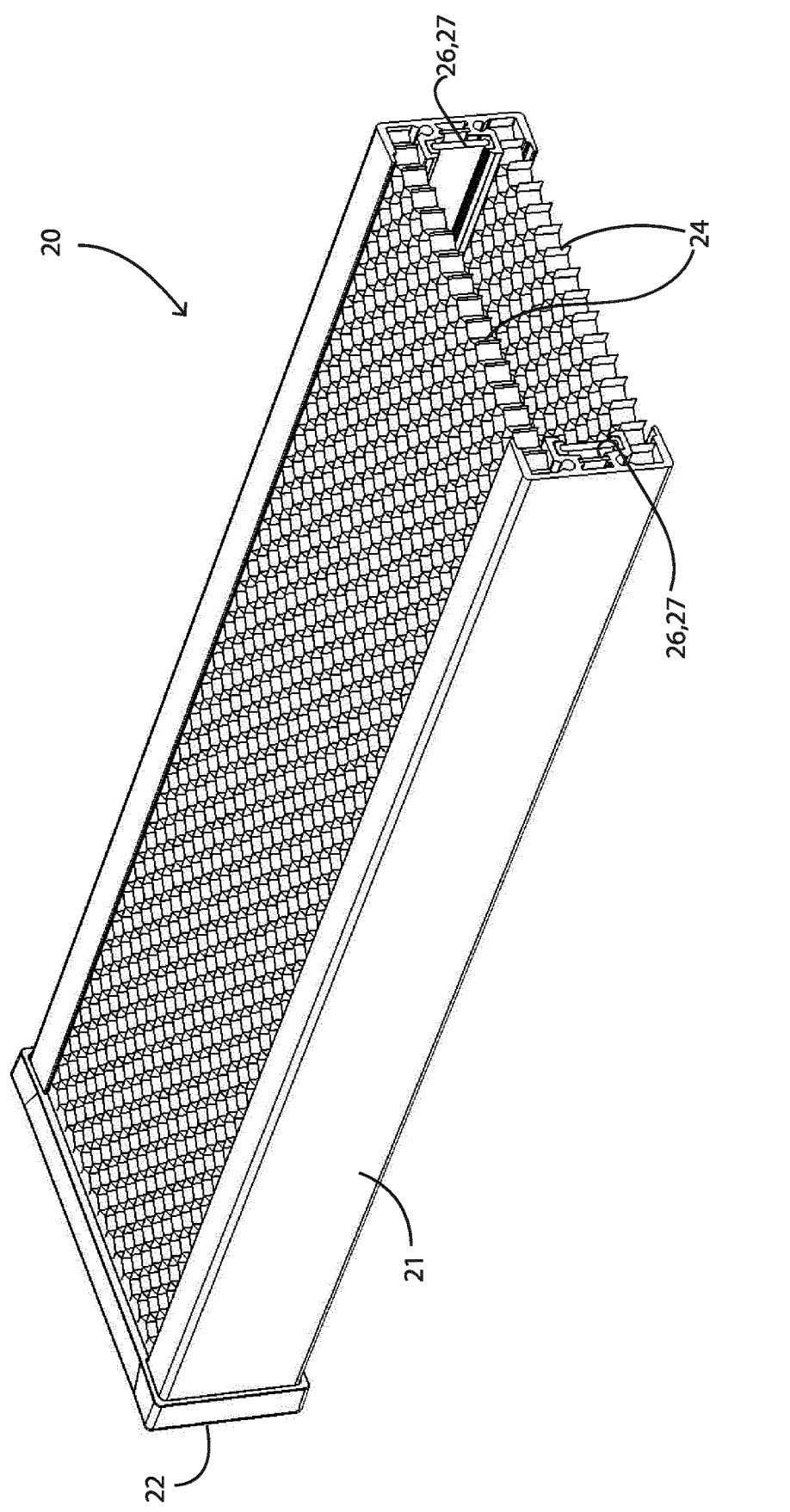
FIG. 5 is a perspective cut-away view of the sanitizer.

FIG. 3 shows an arrangement in which the sanitizer 20 is mounted at a different angle relative to the fan 30, in this case being parallel to the general plane of the top wall of the fan unit 30. In other examples, the sanitizer 20, can be placed anywhere in the airflow path. This illustrates versatility of use of the sanitizer 20.

Figure 6:
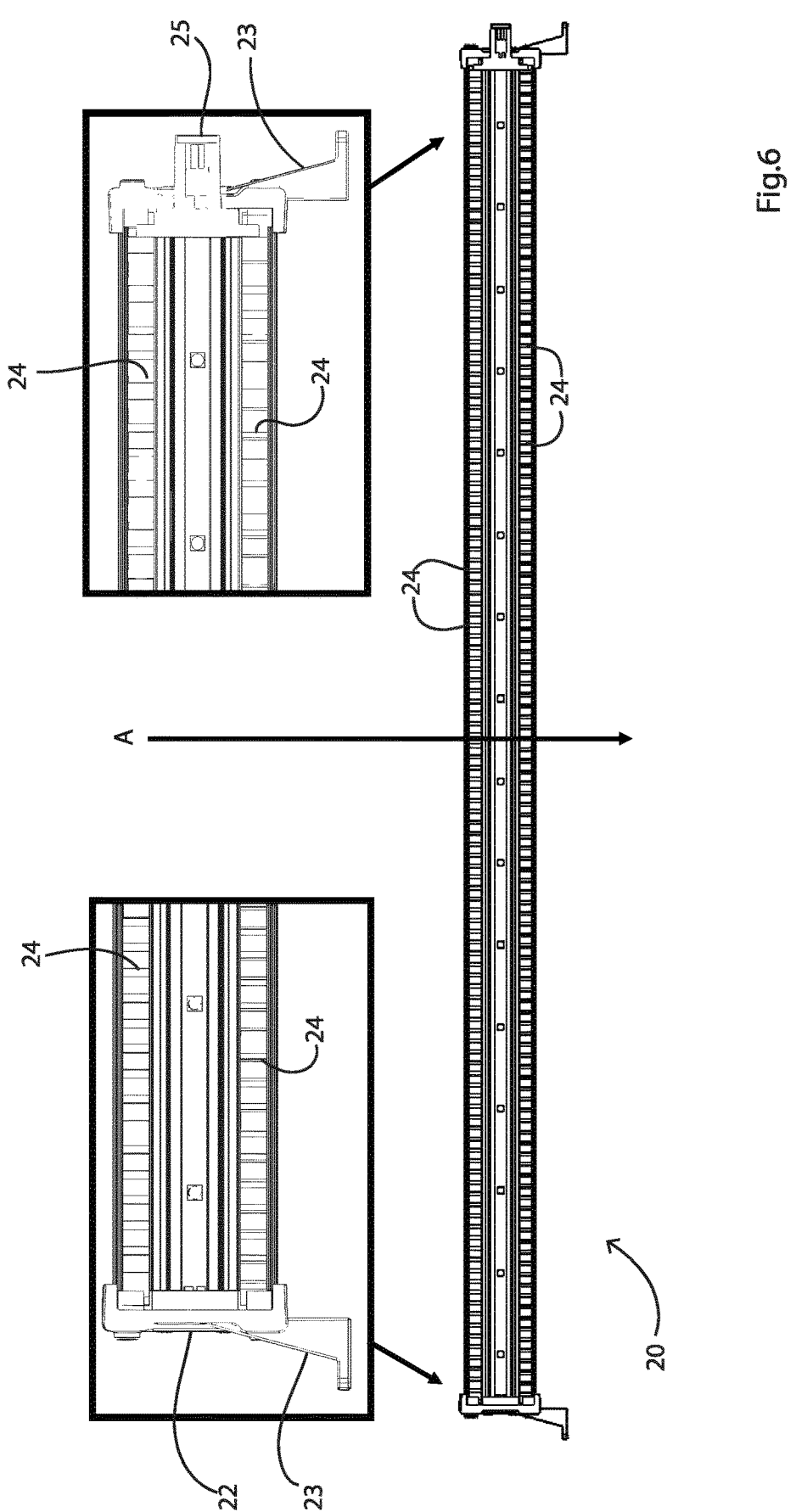
FIG. 6 is a front view of the air sanitizer, with enlarged views of the ends where UV LEDs are located.
Figure 7:
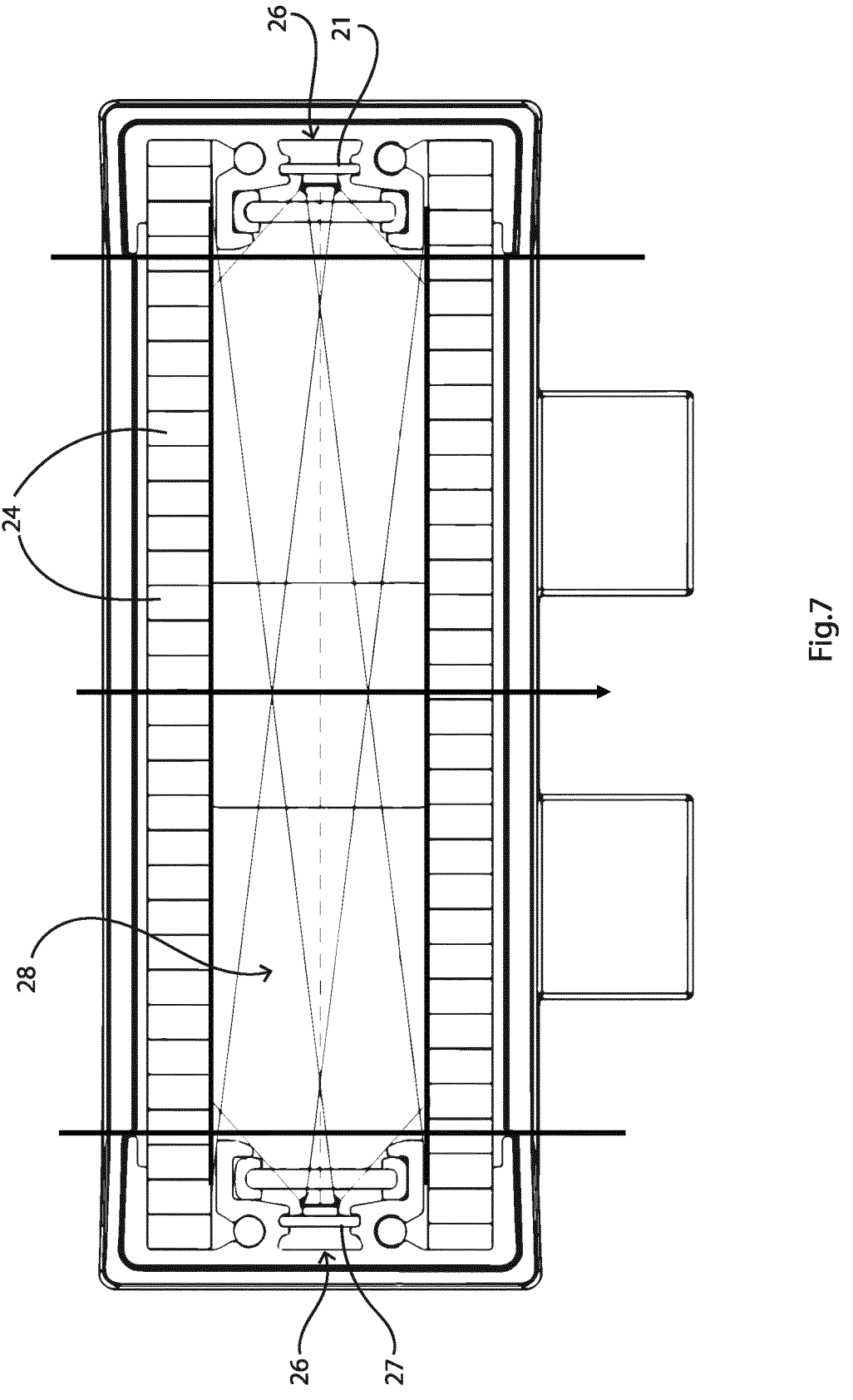
FIG. 7 is a cross-sectional view showing relative positions of the LEDs and of a grille with a titanium dioxide coating which is activated by the UV light.

Referring to FIGS. 4 to 7, the sanitizer 20 comprises a housing 21 with ends 22 having mounting brackets 23 and 25. The housing is of elongate rectangular shape, defining a volume bordered by photocatalytic grilles 24 which are thin metal substrates coated with titanium dioxide nanomaterial, TiO2. A UV light source 27 is mounted at each side, so that they are opposed to each other across the width (11.8 cm). The LEDs 27 are on a substrate 26 with a drive circuit. They emit UV light across the volume, in the vertical direction as it is shown mounted in FIG. 2, and out of the plane of the page as illustrated in FIG. 6, and in the plane of the page as shown in FIG. 7.

The air flow is through the sanitizer 20 as shown by the arrows. The individual coated plates of the grilles 24 are aligned with the air flow. In this case the alignment is by way of each grille having a honeycomb structure, with individual cells 29 aligned with the air flow. In general, it is preferred that the inlet and the outlet have an array of individual conduits of polygonal shape, in this case hexagonal. This provides a large surface area both for air contact with the photocatalytic material, and for light incidence on the TiO2 material to activate it.

In other examples, the arrangement may be different, but in general it is preferred that the light be emitted orthogonally with an angle of divergence across the air path for optimum effectiveness. Where the housing is rectangular it is preferred that the UV light is directed across the width, rather than the length, for optimum effectiveness and intensity.

It is particularly effective that the air is drawn from the display volume through an inlet which is only a minor portion of the area of the base of the case, as this allows it to be focused into an air stream which can be accessed by the UV light and have a high rate of contact with the surfaces of the sanitizer grilles 24. The UV light activates the TiO2, so that the air which comes into contact with the coated surfaces is effectively sanitized in a very efficient manner. This arrangement also avoids penetration of dirt particles into the active components 20, 30, and 40.

In this example, the parameters of the UV LEDs 27 are UVA and within the range of 320 nm-400 nm. The plates 24 are coated with nanoparticles suspended in the TiO2 coating which are less than 50 nm in diameter.

The photocatalytic material is a Titanium Dioxide ($TiO_2$) nanoparticle semiconductor coating in conjunction with a high intensity UV LED activation chamber. This acts as a photoreactor which creates reactive reagents on the surface of the $TiO_2$ which in turn produce reactive cleaning oxygen species, such as hydroxyl radicals ($\cdot OH$), hydrogen peroxide ($H_2O_2$), superoxide radicals ($O_2\cdot{-}$) or hydroperoxyl radicals.

The arrangement illustrated is that the coated surfaces are substantially orthogonal to the axis between the opposed light sources 27, so that the field of emission includes a direction at an acute angle to the surfaces. This provides an optimum combination of contact with air flowing through the grilles and direct UV light incidence for TiO2 activation, the UV emission being shown by the arrows 28 in FIG. 5.

As illustrated, the LED light sources 27 are advantageously arranged to emit light which is directly incident on some of the TiO2 surfaces 24, and indirectly incident by way of reflection on other surfaces. This is aided by the fact that the substrates 24 are substantially orthogonal to the optical axis of the light sources 27, but are spaced from the axis so that diverging light is directly incident on some of the coated surfaces. In general, it is preferred that the angle of emission of the LEDs 27 is across +45° to −45°.

Figure 8:
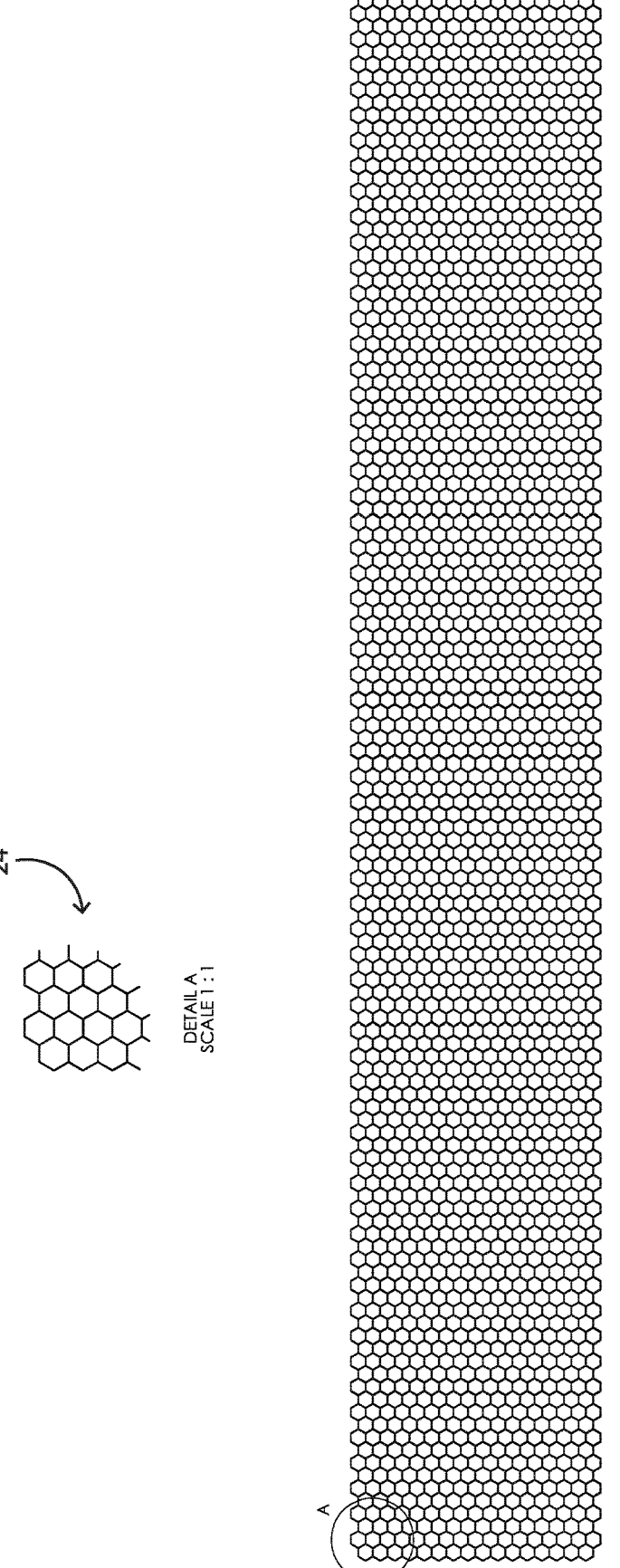
FIG. 8 is a front view of the grille for air inlet and outlet, including an enlarged view.
Figure 8:
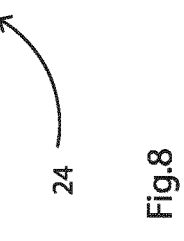
Figure 9:
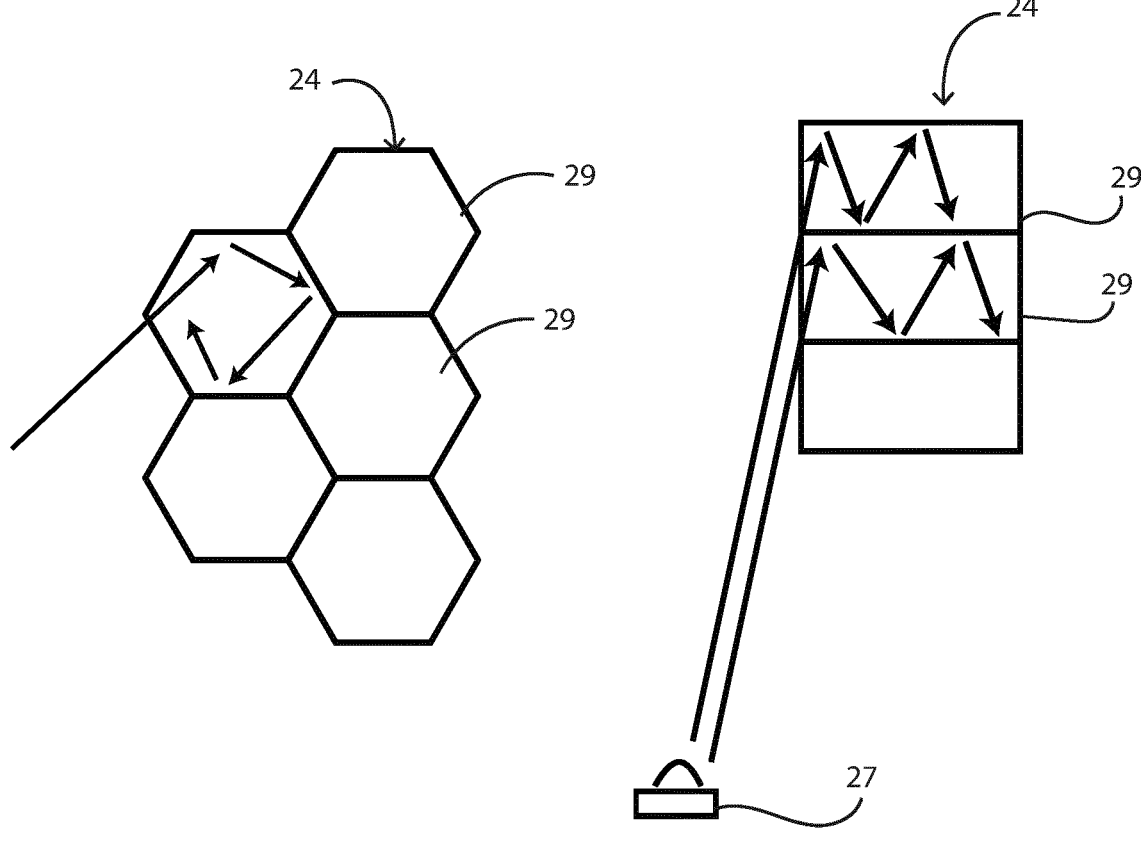
FIG. 9 is a pair of side and end views showing light reflection for optimal incidence on the photocatalytic coating.
Figure 10:
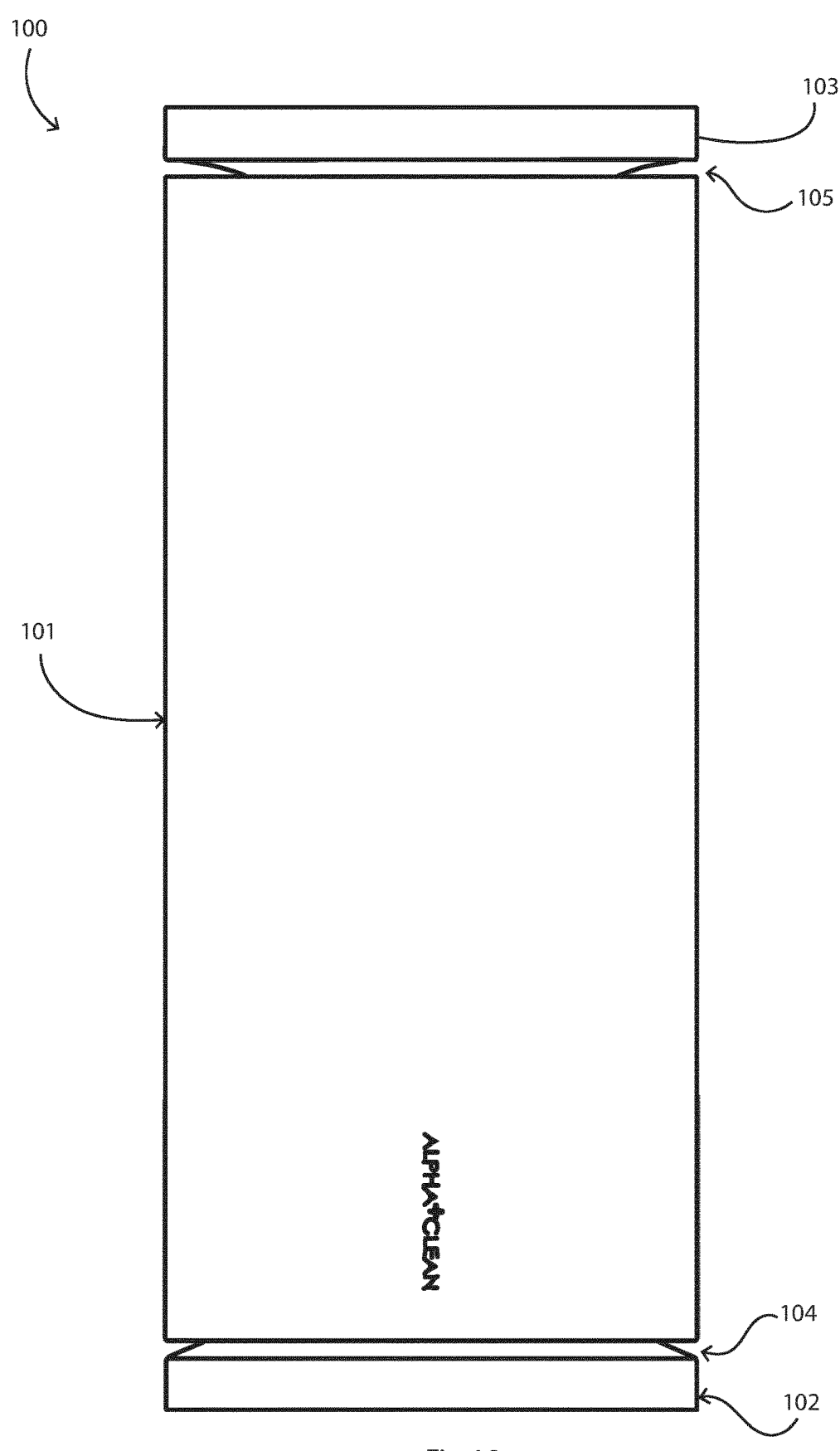
FIG. 10 is a front view of a stand-alone sanitizer of a different embodiment.
Figure 11:
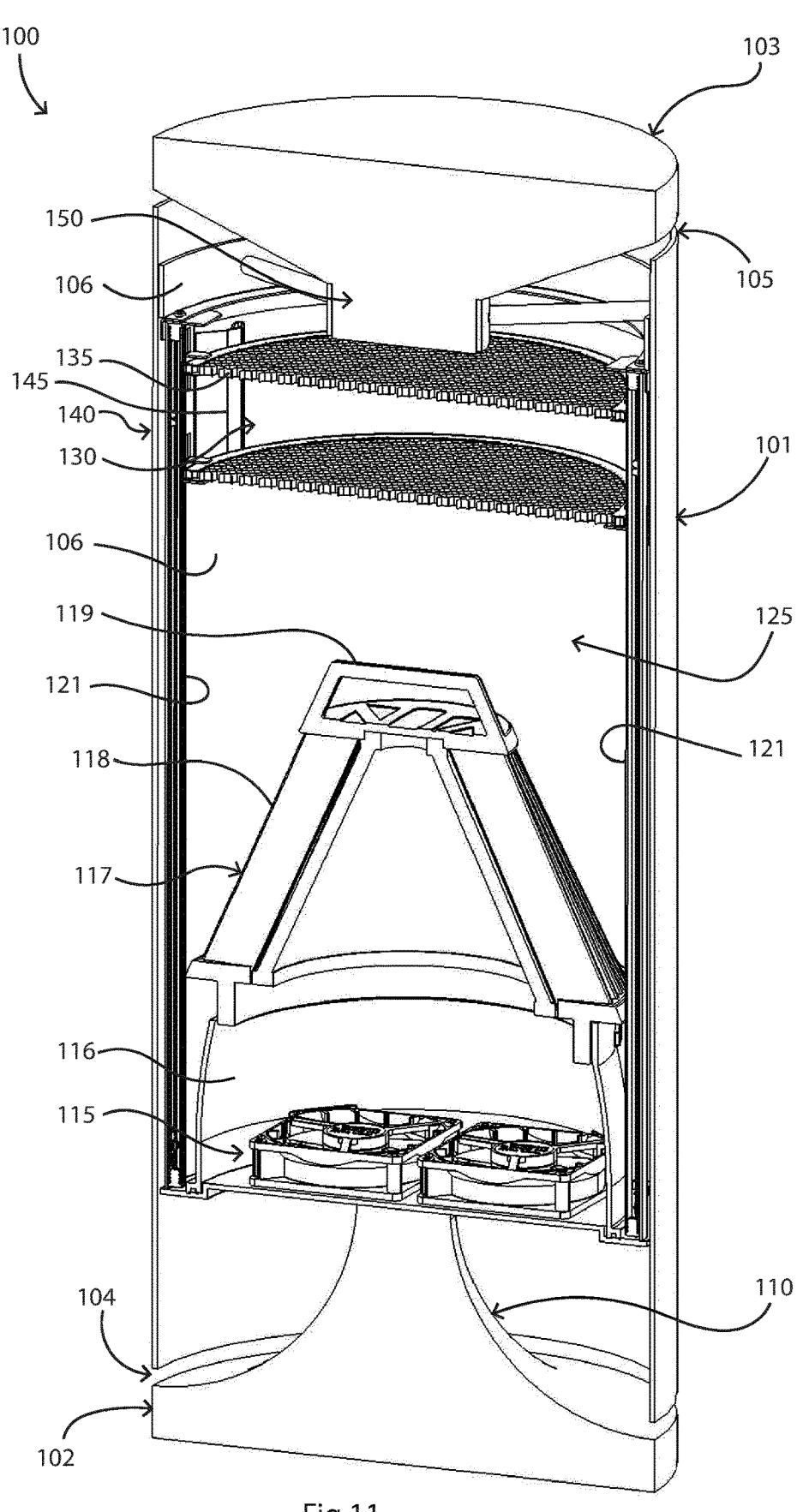
FIG. 11 is a cut-away perspective view showing the internal configuration of this sanitizer.

The honeycomb structure is best shown in FIG. 8, showing the large array of individual conduits or cells 29, and the extent of light incidence on the photocatalytic material is illustrated by the arrows of FIG. 9. The latter diagram shows that light reflects across the path of air through the conduit 29 and, because it is entering a cell 29 at an acute angle, it propagates along the cell with a directional component in the air flow direction (FIG. 9 right hand diagram).

The arrangement of the grilles 24 also provides for turbulence on entry so that any air which does not contact a grille 24 surface upon entry is likely to do so upon exit.

In general, it is preferred that the spectral intensity at the surface of the conduits 29 is greater than 1 mW/cm².

STAND-ALONE EXAMPLES

Referring to FIGS. 10 to 15 an alternative air sanitizer of the invention is illustrated, indicated by the numeral 100. The sanitizer 100 comprises a tubular main body 101 with an internal surface 106, a base 102, and a top 103. There is an annular gap 104 between the base 102 and the main body 101, and this forms an air inlet. Also, there is an annular gap 105 between the housing main body 101 and the top 103, and this forms an outlet for purified air.

The base 102 has the shape of a disc at its lower portion and its upper portion converges in a generally conical portion 110 to form an annular inlet conduit which gradually increases in cross-sectional area leading towards a bank of four fans 115. The fans are aligned with the annular volume or path between the base conical portion 110 and the housing internal surface 106. This helps to streamline air flow, reducing power requirements and fan noise.

The fans 115 direct the inlet air into a generally tubular conduit 116 which has a curved side wall which narrows in the upper/downstream direction about the longitudinal axis of the base 102 and the fan bank 115. The conduit 116 leads into a high-performance HEPA filter 117 which is conical in shape, having a filter side 118 which narrows symmetrically about the longitudinal axis towards an apex portion 119. The filter side walls are configured to filter down to 0.3 μm in this example.

Inlet air flow is directed by the fans 115 through the filter side wall 118 and out into an intermediate chamber 125 between the filter 117 and a first TiO2 photocatalytic grille 130. There is a second TiO2 photocatalytic grille 135 above/downstream of the first grille 130, and in-between there are UV LEDs 140 of 380 nm (the preferred range is 320 nm to 444 nm) wavelength for activating the TiO2 photocatalytic coating on the grilles 130 and 135. This arrangement of LEDs and grilles has a similar principle of operation as that of the sanitizer 1 and the same features and benefits apply, as described above with reference to FIGS. 7 to 9. In this case the LEDs are in a linear array of two short rows extending circumferentially for about 10° around the internal side of the housing 101 on diametrically opposed sides. In other examples, however, them may be spaced such as in groups 90° apart around the circumference, or indeed around the full circumference.

Figure 13:
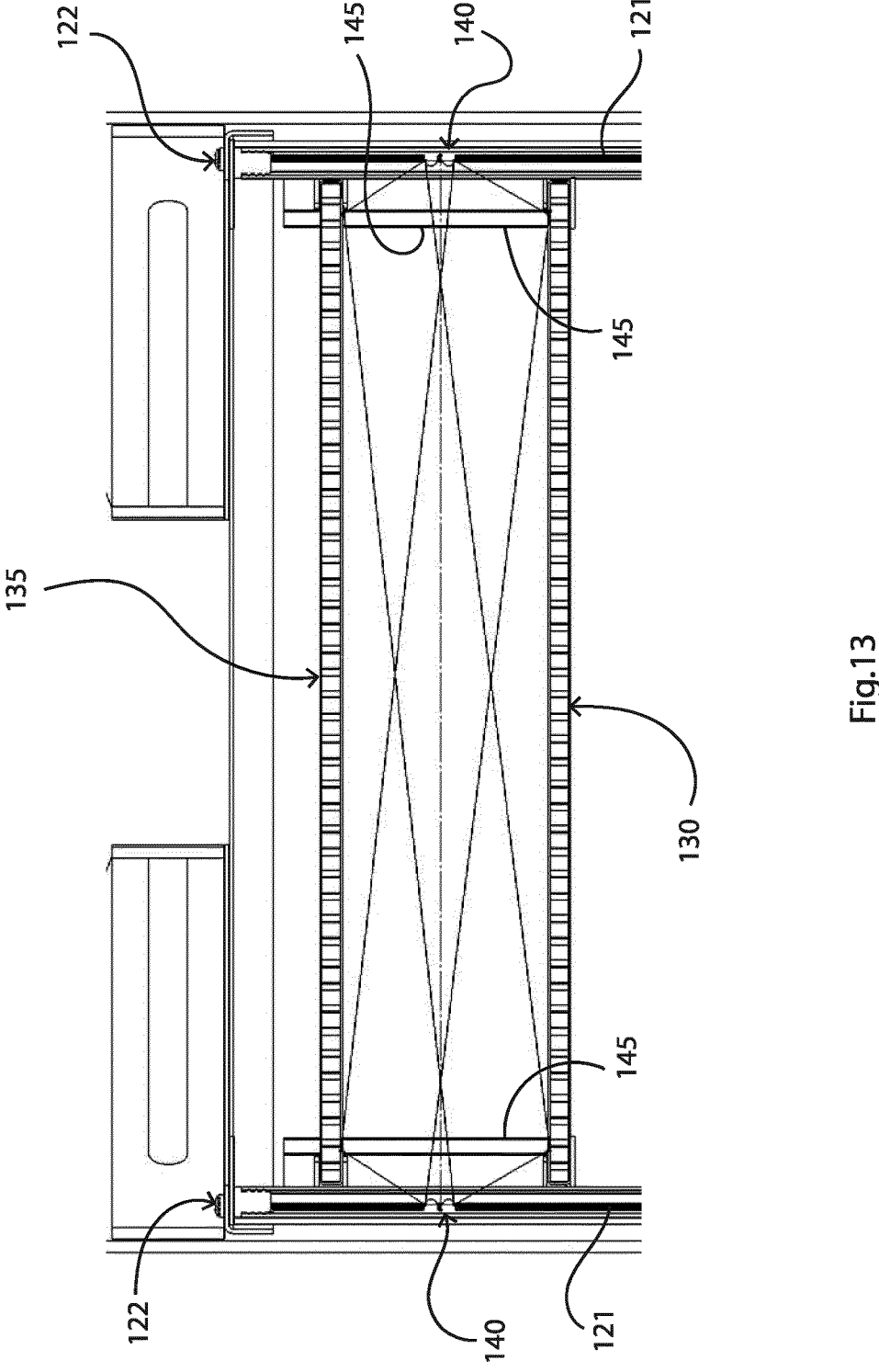
FIGS. 13 and 14 are enlarged views showing LED illumination of a titanium dioxide photo-catalyst on a grille of the sanitizer of FIGS. 10 to 12.

The fan set 115, the filter 117, and the grilles 130 and 135 are inter-connected as a sub-assembly by a pair of arms 121 which extend parallel to the longitudinal axis just inside the housing internal surface 106. These arms support a pair of diametrically opposed brackets 145 which support the grilles 130 and 135 in axially spaced-apart relationship and also act as leaf-spring like spacers to maintain a small (2 to 3 mm) annular gap between the circumferential edges of the grilles 130 and 135 and the housing internal surface 106. FIG. 13 shows in more detail a pair of screw fasteners with resilient washers to provide seals between the top 150 and the arms 121. The assembly which is inter-connected by the arms 121 may be easily removed by un-screwing either the top or the bottom parts. This allows convenient replacement of the filter 17 or other maintenance. It allows modular manufacture and assembly. The drive circuit is also part of this assembly being located in a recessed portion of the fan set 115 base, and power is conducted along elongate PCB tracks on the arms 121.

Figure 12:
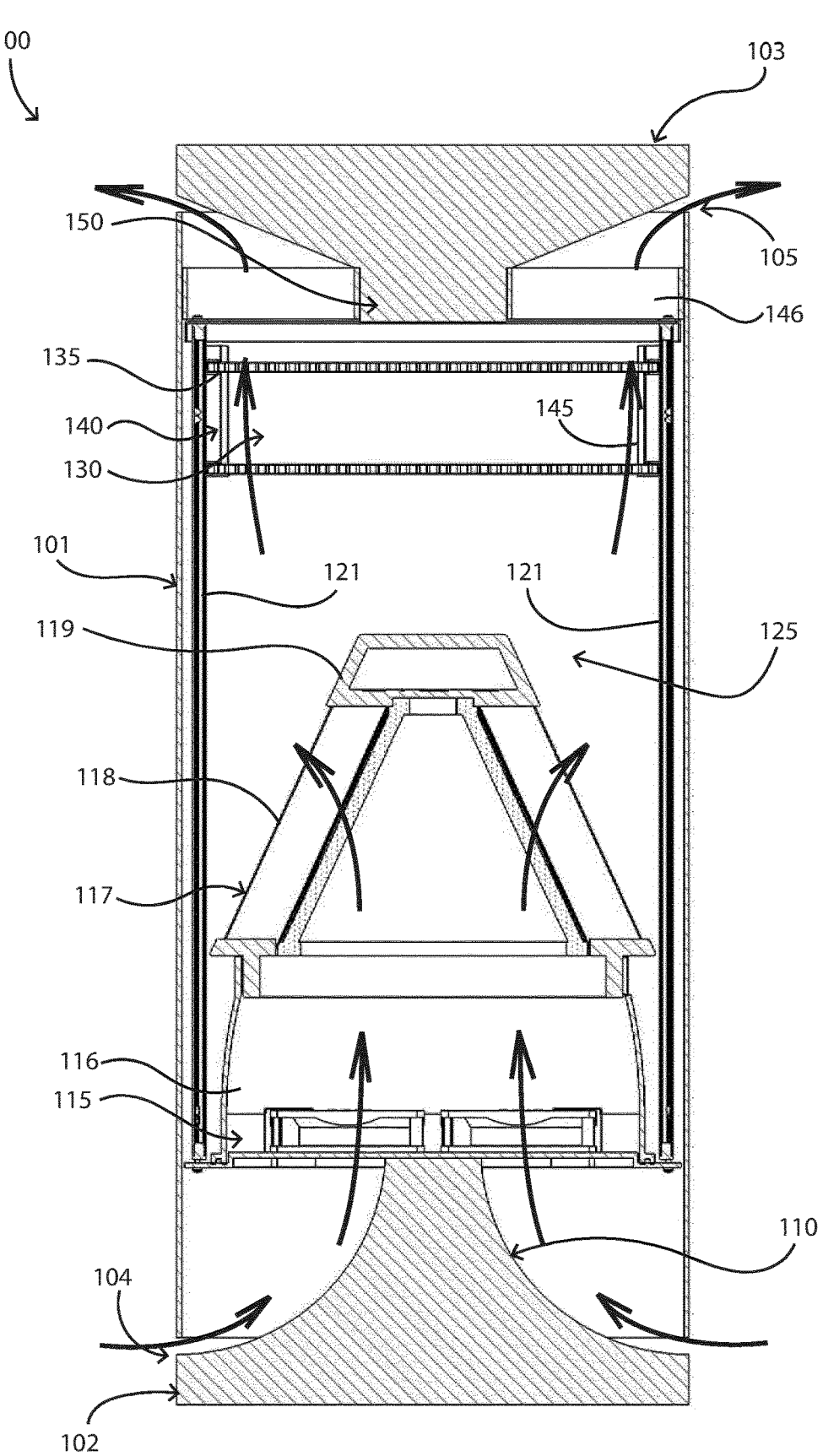
FIG. 12 is a diagram illustrating air flows through the sanitizer of FIGS. 10 and 11.
Figure 14:
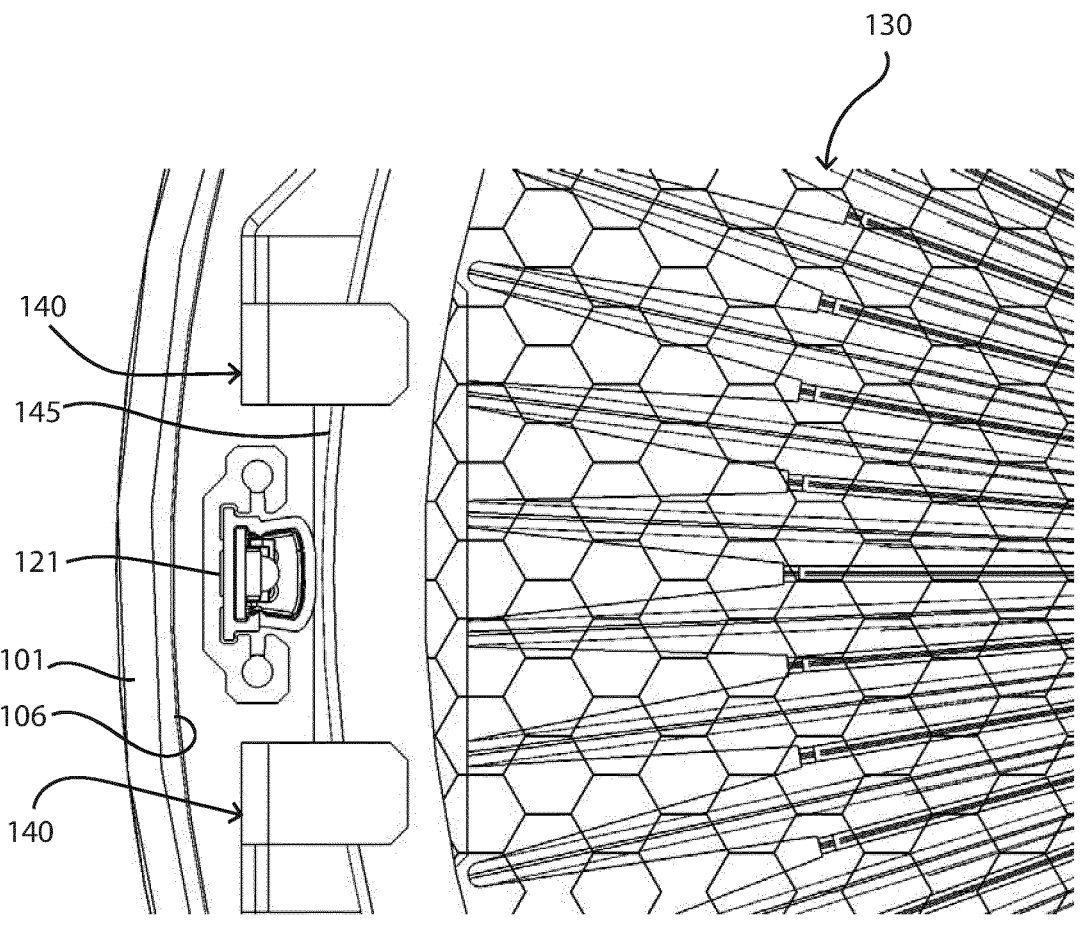

The flows are shown most clearly in FIG. 12. FIGS. 13 and 14 show the interactions of the emitted UV light with the honeycomb grilles, and as noted they are similar to those of the grilles 24 of the sanitizer 1. The sanitized air flows from the honeycomb grilles 130 and 135 into an annular outlet formed by an upstream-extending conical portion 150 of the top 103, and out through the annular outlet 105.

Figure 15:
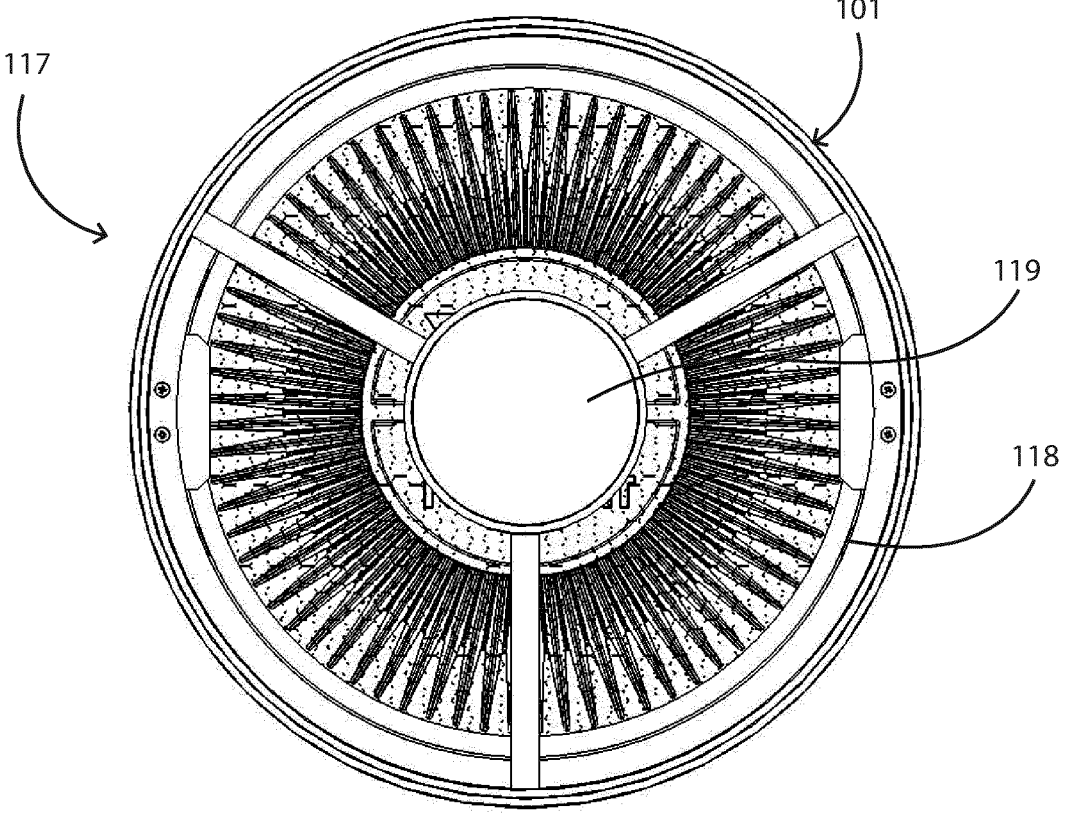
FIG. 15 is an end view of a filter of the sanitizer.

The filter 117 is shown in more detail in FIG. 15. The flow of air is through the side wall 118 which is porous with the filter material. In this case the apex 119 is not porous, and so there is turbulence of the air for flow through the filtering side wall 118 to help promote optimum contact with the filter. However, it is envisaged that in other examples the apex may be of filter material also. A conical shape provides a large surface area, but it is envisaged that if this is not so important the filter may be planar for example. It is also envisaged that there may not be a particulate filter if such filtering is not regarded as important for some applications.

Particulate matter (PM) in the air, whether in solid or liquid form, can affect human health. For example, particles of up to about 2.5 μm represent a hazard, as they are able to enter the bloodstream, and nanoparticles in air can be as small as 0.1 μm right down to 0.001 μm.

Sizes of some well-known bacteria and viruses are as follows:

Influenza A virus: 0.08-0.12 μm

HIV: 0.08 μm

Hepatitis C virus: 0.05 μm

*Mycobacterium tuberculosis:* 1.0 μm

The very common staphylococci (e. g. *Staphylococcus aureus*) are spherical cells of about 1 μm that grow in clusters.

The coronavirus species COVID-2019, MERS-CoV and SARS-CoV range in size from 0.06 μm to 0.2 μm.

Hence, the HEPA filter 17 is very effective at removal of particles down to about 0.3 μm in this example, and the photocatalysis on the surfaces of the grilles 130 and 135 inactivates viruses and bacteria of a very wide range of sizes, rather than just capturing them.

It is very advantageous that the emitted UV is incident on the axially-extending grille surfaces to activate the TiO2 catalyst, and also incident by way of reflection because the LEDs direct the light with a divergence from radial, being incident as shown in FIGS. 7 to 9 and 14. In the sanitizer 100 there is the additional effect of reflection of the emitted UV radiation off the internal surface 106 of the housing 101. These aspects all contribute to very efficient activation of the photo-catalytic material coating the honey comb cells of the grilles 130 and 135.

In one test carried out according to GB/T21551.3-2002 International Standard, *E. coli*, the sanitizer 100 reduced virus amount in a test chamber of 4 m³ volume and with a 200 m³ per hour flow rate to less than 10% in 96 minutes. The dimensions of the sanitizer used in this test were 780 mm×120 mm and there were two rows of LEDs with 24 LEDs on each PCB, with a wavelength of 385 nm.

Use of LEDs to activate the catalyst provides an estimated life up to about 100,000 hours with continuous operation. A controller located in the fan bank 115 provides the drive signals for the fan motors, and it may be configured for operation according to a control scheme. This may be simply according to time, or it may be in response to presence detection. In one example the drive circuit/controller provides conversion from 240V AC or 120V AC to 24V DC. However, any suitable power levels may be used. It is advantageous that similar power levels are used to drive both the LEDS 140 and the fans 115.

The sanitizer 100 may be of any desired physical size, for example 600 mm high and 200 mm in diameter, or 1 m high and 300 mm in diameter. It may be placed at any convenient location n a room such as a doctor's or dentist's surgery or a fitness training room. Power may be from mains or by rechargeable battery.

The sanitizer 100 may also have a wireless (Bluetooth/ WiFi) controller and/or a touch or button user interface on either the outside of the housing 101 or within 102 or 103.

The invention achieves a continuous flow photocatalytic reactor which is especially suited to cleaning of air in rooms of any type and in refrigerated display cases and other cabinets or display units. The cleaning of the airflow is achieved by a photocatalyst reaction on the high-volume surface area of the anodized input and output mesh-structure grilles (or "filters") 24, and 130/135. The filter can be of any substrate material, such as a plastics or a porous aluminium construction. The grille substrate is in this case an aluminium thin foil wall, and the honeycomb core is anodised as a pre-treatment for improved bonding or adhesion to the photo-catalytic coating. The honeycomb arrangement is lightweight, while providing high strength and good rigidity. The aluminium core is a non-combustible material, and the aluminium alloy has good chemical stability, corrosion resistance, and moisture resistance. The aluminium structure also acts as a very effective cooling mechanism for the photocatalyst layer, ensuring that the photocatalytic efficiency remains constant.

The grilles 24 are each a matrix of interconnected honeycomb cores 29 to provide the structure for the volumetric cleaning. The core layer of the honeycomb is a cellular structure, and the array of polygonal cells are regularly arranged, the foil cell walls providing a small cross-sectional area in the direction of the airflow. The aluminium foil provides a thin blade for reducing air resistance. The thickness of the foil is between 5 μm and 25 μm. This thin wall construction can be achieved through the strength achieved by the honeycomb cell arrangement. The length ratio of the honeycomb structure, which is the depth of the cell vs. the cell diameter, is also configured to provide low air resistance and minimise the pressure loss across the filter, while reducing the lateral turbulent airflow through the product.

A polygonal thin wall cell structure, such as a hexagonal, results in an optimal specific or active photocatalytic surface area versus other geometric shapes which would result in an overall lower surface area. The cells could alternatively be arranged as a 3D porous structure.

The air flows through the cells in the normal direction, the LED optical source intensity or primary beam is perpendicular to this airflow and perpendicular to the longitudinal depth of the grille. The polygonal aluminium cell provides or acts as reflective optical trap.

Light incident perpendicular to the cell surface is internally reflected, by the metal surfaces and trapped and re-reflected within the optical cavity as much as possible.

It will be appreciated that the sanitizers provide for delivery of clean air into a room or around products for sale, and this is achieved in a manner which is simple to implement because the cleaning is performed by a modular unit. Also, cleaning efficiency is excellent due to the extent of impingement of air on the activated coatings, and there is an additional cleaning effect arising from direct contact of the UV with the air as it passes through the sanitizer.

The invention is not limited to the embodiments described but may be varied in construction and detail. An air sanitizer of the invention may be used alternatively in other systems in which there is circulating air, for example air-conditioning ducts or on other chiller equipment. The sanitizer 100 may be used by being mounted in an air flow such as that of the sanitizer 1, with suitable support brackets being provided, and possibly with a different housing shape. The latter may be wider and may have and on-axis inlet and/or outlet.

The invention claimed is:

1. An air sanitizer comprising:

a housing with an air inlet and an air outlet;

substrates coated with a photo-catalytic coating for cleaning air which comes into contact with surfaces of the photo-catalytic coating, and a light source comprising LEDs arranged to emit light to be incident on said surfaces to activate the photo-catalytic coating,

9 wherein:

the substrates are arranged as at least one grille, there is an upstream grille and a downstream grille in a direction of air flow; and the LEDs are mounted between said upstream and downstream grilles to emit light across an air flow direction to include the upstream and downstream grilles in the LED fields of emission, the LEDs are arranged to emit light which is directly incident on some of said surfaces of the photo-catalytic coating, and indirectly incident by way of reflection on other surfaces of the photo-catalytic coating, the surfaces on the substrates are substantially orthogonal to an optical axis of the light source, and are spaced from said optical axis so that diverging light is directly incident on at least some of the surfaces and at least some reflect to be incident on other substrate surfaces; and the light emission from the LEDs is at an acute angle to orthogonal to an air flow path between the substrates.

2. The air sanitizer as claimed in claim 1, wherein the light source is a UV light source and the photo-catalytic coating comprises $TiO_2$; and wherein at least some of the LEDs emit with a wavelength in the range of 320 nm to 440 nm; and wherein the LEDs include LEDs of different wavelengths.

3. The air sanitizer as claimed in claim 1, wherein the substrates are in the form of a mesh having an array of air flow conduits extending substantially in an air flow direction; and wherein at least some of the conduits are polygonal in cross-sectional shape.

4. The air sanitizer as claimed in claim 1, wherein the substrates are in the form of a mesh having an array of air flow conduits extending substantially in an air flow direction; and wherein at least some of the conduits are polygonal in cross-sectional shape; and wherein at least some of the conduits are hexagonal, providing a honeycomb structure.

5. The air sanitizer as claimed in claim 1, wherein the substrates have a thickness in the range of 5 μm to 25 μm; and wherein the substrates are separated by an internal air flow path in the range of 5 cm to 50 cm.

6. The air sanitizer as claimed in claim 1, wherein the air sanitizer is adapted for stand-alone operation, comprising at least one fan mounted upstream of said substrates.

7. The air sanitizer as claimed in claim 1, wherein the air sanitizer is adapted for stand-alone operation, comprising at least one fan mounted upstream of said substrates; and wherein the air sanitizer comprises a particulate filter upstream of said substrates.

8. The air sanitizer as claimed in claim 1, wherein the air sanitizer is adapted for stand-alone operation, comprising at least one fan mounted upstream of said substrates; wherein the air sanitizer comprises a particulate filter upstream of said substrates; and wherein the particulate filter has a cone shape, mounted symmetrically about a longitudinal axis of air flow and narrowing in an air flow downstream direction.

9. The air sanitizer as claimed in claim 1, wherein the air sanitizer is adapted for stand-alone operation, comprising at least one fan mounted upstream of said substrates; and wherein the air sanitizer comprises a sanitizer inlet which is annular around an air flow longitudinal axis.

10. The air sanitizer as claimed in claim 1, wherein the air sanitizer is adapted for stand-alone operation, comprising at least one fan mounted upstream of said substrates; and wherein the air sanitizer comprises a sanitizer inlet which is annular around an air flow longitudinal axis; and wherein the sanitizer inlet is formed by a gap between a base and a housing main body.

11. The air sanitizer as claimed in claim 1, wherein the air sanitizer is adapted for stand-alone operation, comprising at least one fan mounted upstream of said substrates; and wherein the air sanitizer comprises a sanitizer inlet which is annular around an air flow longitudinal axis; and wherein there are a plurality of fans arranged around and/or on a longitudinal air flow axis; and wherein the air outlet is annular around an air flow longitudinal axis.

12. The air sanitizer as claimed in claim 1, wherein the air sanitizer is adapted for stand-alone operation, comprising at least one fan mounted upstream of said substrates; and wherein the air sanitizer comprises a sanitizer inlet which is annular around an air flow longitudinal axis; and wherein the air sanitizer comprises a sub-assembly of components which are interconnected and removable from the housing, said sub-assembly of components comprising a fan, a filter, said LEDs, and said substrates; and the sub-assembly of components is interconnected by a plurality of arms which extend parallel to a housing longitudinal axis.

13. The air sanitizer as claimed in claim 1, said substrates comprise a plurality of spaced-apart substrates, wherein the air sanitizer is adapted for stand-alone operation, comprising at least one fan mounted upstream of said substrates; and wherein the air sanitizer comprises a sanitizer inlet which is annular around an air flow longitudinal axis; and wherein a sub-assembly of components comprises at least one bracket which maintains an axial separation between said plurality of spaced-apart substrates and also a gap between said plurality of said spaced-apart substrates and a housing internal surface.

14. The air sanitizer as claimed in claim 1, wherein the air sanitizer is adapted for stand-alone operation, comprising at least one fan mounted upstream of said substrates; and wherein the air sanitizer comprises a sanitizer inlet which is annular around an air flow longitudinal axis; and wherein the LEDs are mounted to emit UV light incident on the substrates and also on a housing internal surface for reflection from said housing internal surface to the substrates.

15. An air sanitizer comprising:

a housing with an air inlet and an air outlet;

substrates coated with a photo-catalytic coating for cleaning air which comes into contact with surfaces of the photo-catalytic coating, and a light source comprising LEDs arranged to emit light to be incident on said surfaces to activate the photo-catalytic coating, wherein the air sanitizer has a substantially rectangular box shape, with a depth dimension which is less than a width dimension, and the width dimension is less than a length dimension, and the LEDs are mounted to emit across the width dimension and the substrates are mounted for air flow through the depth dimension; and wherein the air sanitizer comprises mounting fixtures for mounting to a cooler with a fan, wherein:

the substrates are arranged as at least one grille, there is an upstream grille and a downstream grille in a direction of air flow; and the LEDs are mounted between said upstream and downstream grilles to emit light across an air flow direction to include the upstream and downstream grilles in the LED fields of emission, the LEDs are arranged to emit light which is directly incident on some of said surfaces of the photocatalytic coating, and indirectly incident by way of reflection on other surfaces of the photo-catalytic coating, the surfaces on the substrates are substantially orthogonal to an optical axis of the light source, and are spaced from said optical axis so that diverging light is directly incident on at least some of the surfaces and at least some reflect to be incident on other substrate surfaces; and the light emission from the LEDs is at an acute angle to orthogonal to an air flow path between the substrates.

16. A cabinet or display case comprising a housing for supporting shelves for placement of products, a cooler with a fan for circulating air and delivering cooled air around said products, and an air sanitizer mounted in an air path to or from the cooler, wherein said air sanitizer comprises:

a housing with an air inlet and an air outlet;

substrates coated with a photo-catalytic coating for cleaning air which comes into contact with surfaces of the photo-catalytic coating, and a light source comprising LEDs arranged to emit light to be incident on said surfaces to activate the photo-catalytic coating, wherein the air sanitizer has a substantially rectangular box shape, with a depth dimension which is less than a width dimension, and the width dimension is less than a length dimension, and the LEDs are mounted to emit across the width dimension and the substrates are mounted for air flow through the depth dimension; and wherein the air sanitizer comprises mounting fixtures for mounting to the cooler with the fan, wherein:

the substrates are arranged as at least one grille, there is an upstream grille and a downstream grille in a direction of air flow; and the LEDs are mounted between said upstream and downstream grilles to emit light across an air flow direction to include the upstream and downstream grilles in the LED fields of emission, the LEDs are arranged to emit light which is directly incident on some of said surfaces of the photo-catalytic coating, and indirectly incident by way of reflection on other surfaces of the photo-catalytic coating, the surfaces on the substrates are substantially orthogonal to an optical axis of the light source, and are spaced from said optical axis so that diverging light is directly incident on at least some of the surfaces and at least some reflect to be incident on other substrate surfaces; and the light emission from the LEDs is at an acute angle to orthogonal to an air flow path between the substrates.

17. The cabinet or display case as claimed in claim 16, wherein the air sanitizer is mounted at an inlet of the cooler, and wherein the cooler and the air sanitizer are in a chamber underneath a product volume, being separated by a floor.

\* \* \* \* \*